United States Patent [19]

Arch et al.

[11] Patent Number: 5,082,840
[45] Date of Patent: Jan. 21, 1992

[54] MORPHOLINE COMPOUNDS AND TREATMENT

[75] Inventors: Jonathan R. Arch, Epsam; Norman H. Rogers, Tadworth, both of England

[73] Assignee: Beecham Group p.l.c., Brentford, England

[21] Appl. No.: 399,902

[22] Filed: Aug. 29, 1989

Related U.S. Application Data

[63] Continuation of Ser. No. 166,328, Mar. 10, 1988, Pat. No. 4,914,202.

[30] Foreign Application Priority Data

Mar. 10, 1987 [GB] United Kingdom ................ 8705587
Feb. 12, 1988 [GB] United Kingdom ................ 8803261

[51] Int. Cl.⁵ ................ A61K 31/535; C07D 413/04; C07D 265/30; C07D 265/32
[52] U.S. Cl. ................ 514/233.5; 544/153; 544/106; 544/177; 544/173; 544/163; 544/166; 544/178; 544/174; 544/170; 514/231.2; 514/239.2; 514/239.5; 514/237.8; 514/238.5; 514/238.8; 424/442
[58] Field of Search ................ 544/163, 173, 178, 170, 544/106, 153, 177, 166, 174; 424/442; 514/237.8, 238.5, 238.8, 239.5, 233.5, 231.2, 239.2

[56] References Cited

U.S. PATENT DOCUMENTS 4,404,222 9/1983 Baker et al. ................ 424/304

FOREIGN PATENT DOCUMENTS 0049728 4/1982 European Pat. Off. .
0140359 5/1985 European Pat. Off. .
WO86/05075 9/1986 World Int. Prop. O. .

*Primary Examiner*—John M. Ford
*Attorney, Agent, or Firm*—Hopgood, Calimafde, Kalil, Blaustein & Judlowe

[57] ABSTRACT

A method for increasing the weight gain and/or improving the feed utilization efficiency and/or increasing the lean body mass and/or decreasing birth mortality rate and increasing post-natal survival rate of livestock comprises the administration to livestock of an effective, non-toxic amount of a compound of formula (I), or a veterinarily acceptable acid addition salt thereof:

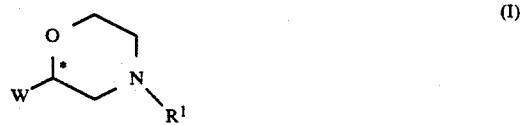

(I)

wherein $R^1$ is phenyl ($C_{1-6}$) alkyl or optionally substituted $C_{1-6}$ alkyl, and W is optionally substituted phenyl, a heterocyclyl group, or phenoxymethyl optionally substituted on the phenyl group. Certain compounds of formula (I) are novel.

11 Claims, No Drawings

MORPHOLINE COMPOUNDS AND TREATMENT

This is a continuation of copending application Ser. No. 01/166,328 filed on 3/10/88, now U.S. Pat. No. 4,914,202.

The present invention relates to derivatives of morpholine, to processes for the preparation of such compounds, to pharmaceutical compositions containing such compounds and the use of such compounds and compositions in medicine and agriculture, and in particular to their use in agriculture.

Morpholine derivatives are described in for example, FR-A-155482, J. Med. Chem. [1986]29, 740, Yakugaku Zasshi [1959]79, 211, Eur. J. Med. Chem. - Chem. Ther. [1976]11. 201 and 443, FR-A-1564792, FR-A-2223007, BE-A-709011, FR-A-2564462, FR-A-2553411, EP-A-138716, FR-A-2471378, EP-A-27695, J. Med. Chem. [1975]18, 873, JP 59204190, FR-A-2285886, and FR-A-2285887. These compounds are described as having, inter alia,. analgesic and opiate antagonist activity.

European Patent Application Publication No. 0,140,359 discloses compounds of formula (A):

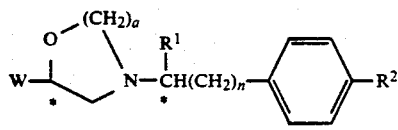

(A)

or a pharmaceutically acceptable acid addition salt thereof, in which

W is phenyl optionally substituted by halogen or trifluoromethyl, or a benzofuran-2-yl group, $R^1$ is hydrogen or methyl, $R^2$ is carboxyl or a group $O-Z-CO_2H$ or an ester or amide thereof; a group $O-E-NR^3R^4$ or a group $O-E-OR^5$, wherein $R^3$, $R^4$ and $R^5$ each represents hydrogen or $C_{1-6}$ alkyl, Z is a $C_{1-6}$ straight or branched alkylene chain, n is 1 or 2, a is 2 or 3, and E is $C_{2-7}$ straight or branched alkylene chain with at least two carbon atoms separating the two heteroatoms in the group $R^2$.

The compounds of EP140359A are described as having anti-hyperglycaemic and/or anti-obesity activity.

International Application Publication No. WO 86/05075 also indicates that the compounds of formula (A) have potential as growth promoters for livestock.

It has now surprisingly been discovered that a particular group of morpholine derivatives show useful potential as growth promoters for livestock.

Accordingly the present invention provides a method for increasing the weight gain and/or improving the feed utilisation efficiency and/or increasing the lean body mass and/or decreasing birth mortality rate and increasing post-natal survival rate of livestock, which method comprises the administration to livestock of an effective, non-toxic amount of a compound of formula (I), or a veterinarily acceptable acid addition salt thereof:

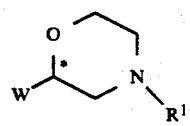

(I)

wherein $R^1$ is phenyl $(C_{1-6})$alkyl or optionally substituted $C_{1-6}$ alkyl, and W is optionally substituted phenyl, a heterocyclyl group, or phenoxymethyl optionally substituted on the phenyl group.

Typically, $R^1$ is $C_{3-6}$ alkyl. Advantageously, $R^3$ is secondary or tertiary alkyl or phenalkyl. Preferably, $R^1$ is $C(CH_3)_3$. Particular values for $R^1$ also include isopropyl Suitable substituents for alkyl include hydroxy.

As used herein substituted phenyl includes phenyl substituted with up to five, preferably up to three, groups selected from halogen, hydroxy, amino, cyano and trifluoromethyl.

It will be appreciated that a hydroxy or amino group may be derivatized in any conventional manner, e.g. acylated.

As used herein heterocyclyl includes single and fused aromatic and nonaromatic 5 to 7 membered rings having up to three heteroatoms in the ring selected from oxygen, nitrogen and sulphur and optionally substituted with up to three groups selected from halogen, hydroxy, amino, and oxo. Typically W is benzofuran-2-yl.

Suitably, W is phenyl substituted by halogen, preferably a chlorine atom. Preferably, W is 3-chlorophenyl, 3,5-dichloro-4-aminophenyl, or 3-cyano-4-aminophenyl.

Suitably, W is a phenyl, 3-chlorophenyl, 3,5-dichloro-4-aminophenyl, 3-trifluoromethylphenyl, 2,5-difluorophenyl, or 3-cyano-4-aminophenyl group.

Suitable pharmaceutically acceptable acid addition salts of compounds of formula (I) include salts formed with a pharmaceutically acceptable acid such as hydrochloric acid, hydrobromic acid, orthophosphoric acid, sulphuric acid, methanesulphonic acid, toluenesulphonic acid, acetic acid, propionic acid, lactic acid, citric acid, fumaric acid, malic acid, succinic acid, salicylic acid or acetylsalicylic acid.

The compounds of formula (I) have an asymmetric carbon atom, marked with an asterisk in the formula, and $R^1$ may also include one or more asymmetric carbon atoms. These compounds may, therefore, exist in at least two stereoisomeric forms. The present invention encompasses all stereoisomers of the compounds of formula (I) whether free from other stereoisomers or admixed with other stereoisomers in any proportion and thus includes, for instance, racemic mixtures of enantiomers.

The absolute configuration of any compound of formula (I) may be determined by conventional X-ray crystallographic techniques.

Compounds of formula (I) have been found to enhance the production of muscle protein. Accordingly, a further aspect of the invention provides a method for treating conditions associated with an increased protein breakdown, which method comprises administering an effective, non-toxic amount of a compound of formula (I), or a pharmaceutically acceptable acid addition salt thereof, to a human in need thereof. Examples of such conditions include muscular dystrophies and atrophies, cancer cachexia, and are also typically found after surgery, infection, or other trauma.

Compounds of formula (I) may also be used to enhance muscle function, particularly where this is not possible in other ways such as exercise. Examples include peripheral vascular disease in humans and physical conditioning for immobilized racehorses.

In a further aspect of the invention, compounds of formula (I) may be used in the treatment of obesity in human and non-human mammals.

A still further aspect of the invention provides the use of a compound of formula (I) or a pharmaceutically or veterinarily acceptable acid addition salt thereof in the manufacture of a medicament for use in the treatment of conditions associated with an increased protein breakdown in humans, the therapeutic enhancement of muscle function, or the therapeutic treatment of obesity, or a veterinarily acceptable formulation for use in the treatment of livestock to decrease birth mortality rate and increase post-natal survival rate.

A compound of formula (I), or a pharmaceutically acceptable acid addition salt thereof, may be prepared by reacting a compound of formula (II):

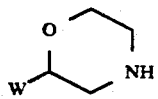

(II)

wherein W is as defined in relation to formula (I) or an acid addition salt thereof, with a compound of formula (III):

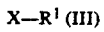 (III)

wherein $R^1$ is as defined in relation to formula (I) and X is a leaving group, such as a halogen or an alkylsulphonyloxy or arylsulphonyloxy group; and thereafter, if required, preparing a pharmaceutically acceptable acid addition salt of the compound of formula (I).

Preferably X is chlorine or bromine or a p-toluenesulphonyloxy group.

Preferably, $R^1$ is a $C_{1-6}$ alkyl group other than $C(CH_3)_3$.

When a compound of formula (II) is reacted with a compound of formula (III) wherein X is halogen or an alkylsulphonyloxy or arylsulphonyloxy group the reaction is generally carried out in the presence of an inorganic base in any suitable solvent preferably at an elevated temperature, for example in the presence of potassium carbonate in refluxing acetone.

A compound of formula (I), or a pharmaceutically acceptable acid addition salt thereof, may also be prepared by cyclising a compound of formula (IV).

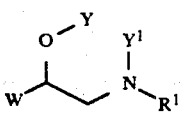

(IV)

wherein W and $R^1$ are as defined in relation to formula (I), and either:

Y is H and $Y^1$ is —(CH$_2$)$_2$—OH, or
Y is —(CH$_2$)$_2$—X wherein X is a leaving group and $Y^1$ is H; and thereafter, if required preparing a pharmaceutically acceptable acid addition salt of the compound of formula (I).

Suitably, X represents a halogen atom, such as a Chlorine atom, or an activated hydroxyl group such as mesylate, tosylate or triflate.

Suitably, when Y is H and $Y^1$ is —(CH$_2$)$_2$—OH, the cyclisation is generally conducted in the presence of a conventional dehydrating reagent such as sulphuric acid.

Suitably, when Y is —(CH$_2$)$_2$—X and $Y^1$ is hydrogen the cyclisation reaction is generally conducted in the presence of an inorganic base in an organic solvent suitably at elevated temperatures; for example by using sodium ethoxide in refluxing ethanol, or potassium carbonate in refluxing acetone.

A compound of formula (I), or a pharmaceutically acceptable acid addition salt thereof, may also be prepared by reducing a compound of formula (V):

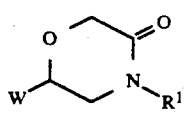

(V)

wherein W is as defined in relation to formula (I); and thereafter, if required, preparing a pharmaceutically acceptable acid addition salt of the compound of formula (I).

The abovementioned reduction of a compound of formula (V) may be carried out using any suitable conventional method of reduction.

Conveniently the reduction is carried out using borane-methyl sulphide or lithium aluminium hydride as the reducing agent in a solvent such as tetrahydrofuran.

A compound of formula (IV), wherein Y is hydrogen and $Y^1$ represents —(CH$_2$)$_2$—OH, may be prepared by reacting a compound of formula (VI):

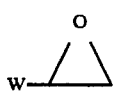

(VI)

wherein W is as defined in relation to formula (I), with a compound of formula (VII):

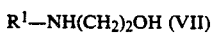

wherein $R^1$ is as defined in relation to formula (IV).

The reaction between the compounds of formulae (VI) and (VII) may be carried out in any suitable solvent preferably an alcoholic solvent, most preferably at an elevated temperature, for example in refluxing butanol.

A compound of formula (IV) wherein Y is—(CH$_2$)$_2$—X and $Y^1$ is hydrogen may be prepared using methods analogous to those disclosed in EP140359A.

The compound of formula (V) may be prepared by cyclising a compound of formula (VIII):

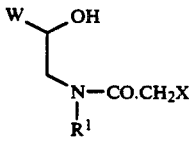

(VIII)

wherein W, $R^1$ and X are as defined in relation to formula (IV).

The abovementioned cyclisation of a compound of formula (VIII) may be carried out under analogous conditions to those used for cyclising a compound of formula (IV) wherein Y is —(CH$_2$)$_2$—X and $Y^1$ is hydrogen.

Compounds of formulae (II) and (III) are known compounds or can be prepared from known compounds by using conventional procedures.

Compounds of formulae (VI), (VII) and (VIII) are either known compounds or may be prepared by methods analogous to those used to prepare known compounds.

The acid addition salts of compounds of formula (I) may be produced by treating the compound of formula (I) with the appropriate acid.

Compounds of formula (I) and salts, thereof, produced by the above processes, may be purified by conventional methods.

Enantiomers of compounds of formula (I) may be prepared by resolving a mixture of stereochemical isomers of a compound of formula (I) by conventional means, such as by the use of an optically active acid as a resolving agent, or by suitable stereoselective synthesis.

Suitable optically active acids which may be used as resolving agents are described in 'Topics in Stereochemistry', Vol. 6, Wiley Interscience, 1971, Allinger, N.L., and Eliel, W.L. Eds.

As indicated above the compounds of formula (I), and the pharmaceutically acceptable acid addition salts thereof, have useful medicinal properties.

A compound of formula (I) or a pharmaceutically acceptable acid addition salt thereof (hereinafter 'the drug') may be administered as the pure drug, however, it is preferred that the drug be administered as a pharmaceutical composition also comprising a pharmaceutically acceptable carrier.

As used herein the terms 'pharmaceutical' and 'pharmaceutically' embrace compounds, compositions and ingredients for both human and veterinary use.

Usually the compositions will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or the like.

Typical carriers may, therefore, comprise such agents as microcrystalline cellulose, starch, sodium starch qlycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 1000 mg of the drug, more usually 0.1 to 500 mg and favourably 0.1 to 250 mg.

In the treatment of the abovementioned conditions associated with an increased protein breakdown the drug may be taken in doses, such as those described above, one to six times a day in a manner such that the total daily dose for a 70 kg adult will generally be about 0.1 to 6000 mg, and more usually about 1 to 1500 mg.

As indicated above, the compounds of formula (I) also have valuable veterinary properties.

Suitably, the invention provides a method for increasing the weight gain and/or improving the feed utilisation efficiency and/or increasing the lean body mass of livestock.

Suitably, the invention also provides a method for decreasing birth mortality rate and increasing the post-natal survival rate of livestock.

Suitable livestock include poultry (especially turkeys and chickens), cattle, pigs, sheep, deer, rabbits, or goats.

Suitably, the invention provides a method for increasing the weight gain and/or improving the feed utilisation efficiency and/or increasing the lean body mass of poultry, (especially turkeys and chickens), cattle, pigs or sheep; particularly of cattle, pigs or sheep.

It will be understood that the advantages provided by the present invention relating to the decrease in birth mortality rate and increase in post-natal survival rate are provided by administration to female parent livestock or the newly-born livestock, the decrease in birth mortality rate and increase in post-natal survival rate relating primarily to the newly born livestock.

In a particular aspect, the present invention provides a method for decreasing birth mortality rate and increasing post-natal survival rate of livestock, which method comprises the administration to pregnant livestock of an effective, non-toxic amount of a compound of formula (I), or a veterinarily acceptable acid addition salt thereof.

Suitable pregnant livestock include pregnant cows, sows and ewes.

The method of the invention is particularly suitable for decreasing the birth mortality rate and increasing the post-natal survival rate of lambs by administration to pregnant ewes.

The present invention also encompasses the use of a compound of formula (I), or a veterinarily acceptable acid addition salt thereof, for the manufacture of a veterinarily acceptable formulation for decreasing the birth mortality rate and increasing the post-natal survival rate of livestock.

A compound of formula (I), or a veterinarily acceptable acid addition salt thereof will normally be administered orally, although non-oral modes of administration for example injection or parenteral, e.g. subcutaneous, implantation, are also envisaged, as is administration via a rumen delivery system in the case of ruminants.

The particular formulation used will depend upon the chosen mode of administration but in general will be that used conventionally in the mode of administration chosen.

In addition there is provided a veterinarily acceptable formulation, for increasing the weight gain and/or improving the feed utilisation efficiency and/or increasing the lean body mass and/or decreasing birth mortality rate and increasing post-natal survival rate of livestock which formulation comprises a compound of formula (I), or a veterinarily acceptable acid addition salt thereof, and a veterinarily acceptable carrier therefor.

Suitably, the compound is administered in the feed-stuff or drinking water provided for the livestock. Conveniently the compound is administered in feed-stuff or drinking water comprising from $10^{-3}$ ppm $-500$ ppm of the total daily feed or water intake, more usually 0.01 ppm to 250 ppm, suitably less than 100 ppm for example 0.1 to 10 ppm.

For administration in feed-stuff the compound is conveniently formulated as a premix in association with a suitable carrier Accordingly, the present invention also provides a veterinarily acceptable premix formulation comprising a compound of formula (I), or a veterinarily acceptable acid addition salt thereof, in association with a veterinarily acceptable carrier therefor.

Suitable carriers are inert conventional agents such as powdered starch. Other conventional feed-stuff premix carriers may also be employed.

Suitably the premix formulation will contain from about 0.001% to about 95% by weight of the compound, more typically about 0.001% to 20% by weight of the compound.

When the compound is administered by non-oral mode for example by injection or implantation, any conventional formulation may be used to administer the compounds; suitably, the invention comprises the administration of from about 0.1 μg/kg to about 50 mg/kg of the compounds, more usually about 1 μg/mg to about 25 mg/kg preferably less than 10mg/kg.

The formulations of the invention may be prepared by any conventional process; for example a premix formulation may conveniently be prepared by dissolving a compound in any suitable solvent, such as methanol; blending the resulting solution and carrier to the required proportions and removing the solvent by drying under appropriate conditions.

The veterinary formulations of the invention may include a further active agent in addition to the compound of the invention, such as antibiotic compounds conventionally used as growth promoters.

Within the above indicated dosage range, no adverse toxicological effects have been observed with the pharmaceutically acceptable compounds of the invention.

Certain compounds of formula (I) are novel per se, and these novel compounds and their pharmaceutically and veterinarily acceptable acid addition salts, the above processes for their preparation, pharmaceutical and veterinary compositions containing the same, and their use in the methods of the invention, and the manufacture of medicaments for use in the methods of the invention, form a particular aspect of the invention.

In particular, the compounds of Examples 1, 4 to 8, 10 and 12 hereinbelow are believed to be novel.

The present invention will now be illustrated with reference to the following Examples, which do not limit the scope of the invention in any way.

EXAMPLE 1

2-[3-Chlorophenyl]-4-[1,1-dimethylethyl]morpholine hydrochloride

Borane-methyl sulphide (0.5 ml) was added dropwise, under nitrogen, to a stirred solution of 2-[3-chlorophenyl]-4-[1,1-dimethylethyl]-5-oxo-morpholine (0.85g) in dry tetrahydrofuran (40 ml). The mixture was heated under reflux for 2 h., cooled, treated with methanol (5 ml) and heated for 1 hr. The resulting solution was cooled, treated with hydrogen chloride and evaporated to give 2-[3-chlorophenyl]-4-[1,1-dimethylethyl]morpholine hydrochloride as a white solid (0.54g), m.p. 223–8° C. (ethyl acetate).

$^1$H NMR (d$_6$-DMSO), ppm 1.38(9H,s), 3.03–3.14(2H,m), 3.51(2H,t), 4.13–4.23(2H,m collapses to a doublet with D$_2$O), 5.11(1H,d), 7.37–7.45(3H,m),7.55(1H,s), 11.29(1H, broad disappears with D$_2$O).

$^{13}$C NMR (d$_6$-DMSO), ppm 23.7(CH$_3$), 44.93(CH$_2$), 49.88(CH$_2$), 63.43(CH$_2$), 63.54(C), 74.01(CH), 125.54(CH), 126.57(CH), 128.55(CH), 130.41(CH), 133.21(C), 140.05(C).

EXAMPLE X1

N-[1,1-Dimethylethyl]-3-chloro-α-hydroxybenzeneacetamide

Dicyclohexylcarbodiimide (11.0Sg) was added in portions to a cooled, stirred mixture of 3-chloro-α-hydroxybenzeneacetic acid (10g), 1,1-dimethylethanamine (3.92g, 5.63ml) and 1-hydroxybenzotriazole (7.24g) in dry dimethylformamide (100ml). The mixture was stirred at ambient temperature for 20h., filtered and the filtrate evaporated. The residual oil was taken up in ethyl acetate, filtered, and the filtrate washed sequentially with sodium carbonate solution, hydrochloric acid (2N) and water. The organic layer was dried (MgSO$_4$), filtered, and evaporated to an oil which was chromatographed on silica. Elution with chloroform gave N-[1,1-dimethylethyl]-3-chloro-α-hydroxybenzeneacetamide, 1.71g, as an oil which crystallized on standing, m.p. 93–99° C.

$^1$H NMR (d$_6$-DMSO], ppm 1.25(9H,s), 4.86(1H,d, collapses to a singlet with D$_2$O), 6.23(1H,d, disappears with D$_2$O), 7.29–7.37(3H,m+1H, broad, disappears with D$_2$O), 7.45(1H,s).

EXAMPLE X2

3-Chloro-α-[[1,1-dimethylethyl]amino]methyl]benzenemethanol

Borane-methyl sulphide (2.15g, 2.7ml, 4 equivs.) was added dropwise, under nitrogen, to a stirred solution of N-[1,1-dimethylethyl]-3-chloro-α-hydroxybenzene acetamide (1.71g) in dry tetrahydrofuran. The resulting solution was stirred and heated under reflux for 2h., cooled, and treated with methanol (1ml). The reaction mixture was heated under reflux for 1 h., cooled, treated with methanolic hydrogen chloride, and the solvent evaporated to give 3-chloro-α-[[[1,1-dimethylethyl]amino]methyl]benzenemethanol hydrochloride salt, 1.5g, m.p. 165–175° C.

$^1$H NMR (d$_6$-DMSO), ppm (hydrochloride)

1.32(9H,s), 2.85(1H,m, collapses to dd with D$_2$O), 3.05 (1H,m, collapses to dd with D$_2$O), 5.04(1H,ddd, collapses to dd with D$_2$O), 6.34(1H,d, disappears with D$_2$O), 7.3–7.46(3H,m), 7.50(1H,s), 8.59(1H, broad m, disappears with D$_2$O), 9.50(1H, broad m, disappears with D$_2$O).

EXAMPLE X3

α-Chloro-N-[2-(3-chlorophenyl)-2-hydroxyethyl]-N-[1,1-dimethylethyl]acetamide

Chloroacetyl chloride (0.21g, 0.15ml) in dichloromethane (5ml) was added dropwise, under nitrogen to a stirred, ice-cooled solution of 3-chloro-α-[[[1,1-dimethylethyl]amino]methyl]benzenemethanol (0.5g) and triethylamine(0.38g, 0.53ml) in dichloromethane (40ml). The reaction mixture was stirred at ambient temperature for 2h., washed with hydrochloric acid (2N), brine, dried (MgSO$_4$), evaporated and chromatographed on silica. Elution with chloroform gave α-chloro-N-[2-(3-chlorophenyl)-2-hydroxyethyl]-N-[1,1- dimethylethyl]acetamide as a colourless oil.

$^1$H NMR (CDCl$_3$), ppm 1.47(9H,s), 3.45(2H,d), 3.9(1H, broad), 4.0(1H,d), 4.44(1H,d), 4.85(1H,t), 7.2–7.4(4H,m).

EXAMPLE X4

2-[3-Chlorophenyl]-4-[1-1-dimethylethyl]-5-oxo-morpholine

α-Chloro-N-[2-(3-chlorophenyl)-2-hydroxyethyl]-N-[1,1-dimethylethyl]acetamide (1.3g) in ethanol (15ml) was added to a stirred solution of sodium ethoxide [sodium (0.1g) in ethanol (40ml)]. The resulting solution was stirred and heated under reflux for 16h., cooled, and the solvent evaporated. The residue was partitioned between ethyl acetate and water, the organic layer separated, dried (MgSO$_4$) and evaporated to give an oil which was chromatographed on silica. Elution with chloroform gave 2-[3-chlorophenyl]-4-[1-1-dimethylethyl]-5-oxo-morpholine as an oil, 0.85g.

$^1$H NMR (CDCl$_3$), ppm 1.38(9H,s), 3.1–3.6(2H,m), 4.15(2H,s), 4.55(1H,dd), 7.15–7.4(4H,m).

EXAMPLE 2

4-1,1-Dimethylethyl]-2-phenylmorpholine hydrochloride

4-[1,1-Dimethylethyl]-2-phenylmorpholine was prepared from 4-[1,1-dimethylethyl]-5-oxo-2-phenylmorpholine and borane-methyl sulphide by an analogous procedure to that described in Example 1. After purification by column chromatography on silica using 0—>8% methanol in dichloromethane as eluant, the resultant oil was converted to its hydrochloride salt, m.p. 208–210° C., (ethyl acetate).

$^1$H NMR (d$_6$-DMSO), ppm 1.4 (9H,s), 2.7–3.6(4H,m), 4.0–4.35(2H,m), 5.15(1H,d), 7.4–7.6(5H,m), 11.2–11.8(1H,broad, disappears with D$_2$O).

EXAMPLE 3

2-[3-Chlorophenyl]-4-1-methylethyl]morpholine hydrochloride

The title compound, m.p. 224–5° C. (methanol-ethyl acetate), was prepared from 2-[3-chlorophenyl]-4-[1-methylethyl]-5-oxomorpholine and borane-methyl sulphide by an analogous procedure to that described in Example 1.

$^1$H NMR (d$_6$-DMSO), ppm 1.4(6H,d), 2.8–3.7(5H,complex), 4.05–4.2(2H,m), 5.1(1H,d), 7.3–7.65(4H,m), 11.4–12.05(1H,broad, disappears with D$_2$O).

EXAMPLE 4

2-4-Amino-3,5-dichlorophenyl]-4-[1,1-dimethylethyl] morpholine hydrochloride

The title compound, m.p. 283–4° C. (d) (methanol-ethyl acetate), was prepared from 2-[4-amino-3,5-dichlorophenyl]-4-[1,1-dimethylethyl]-5-oxo morpholine and borane-methyl sulphide by an analogous procedure to that described in Example 1.

$^1$H NMR (d$_6$-DMSO), ppm 1.4(9H,s), 2.85–3.6(4H,m), 4.0–4.3(2H,m), 4.9(1H,d), 5.6(2H,broad s, disappears with D$_2$O), 7.35(2H,s), 11.0–11.6(1H,broad, disappears with D$_2$O).

EXAMPLE 5

[4-[1,1-Dimethylethyl]-2-[3-trifluoromethylphenyl] morpholine hydrochloride

The title compound, m.p. 227–9° C. (d) (methanol(-trace)-diethyl ether - hexane), was prepared from 4-[1,1-dimethylethyl]-5-oxo-2-[3-trifluoromethylphenyl] morpholine and borane-methyl sulphide by an analogous procedure to that described in Example 1.

$^1$H NMR (d$_6$-DMSO), ppm 1.4(9H,s), 2.75–3.85(4H,m), 4.05–4.45(2H,m), 5.3(1H,d), 7.6–7.95(4H,m), 11.5–12.0 (1H,broad, disappears with D$_2$O).

EXAMPLE 6

2-[4-Amino-3-cyanophenyl]-4-[(1-methylethyl]morpholine monohydrochloride

Borane in tetrahydrofuran (1.0 M solution; 7.5 ml) was added dropwise, at ambient temperature, to a stirred solution of 2-[4-amino-3-cyanophenyl]-4-[1-methylethyl]-5-oxomorpholine (0.83g) in dry tetrahydrofuran (60 ml) under nitrogen. The mixture was then heated under reflux with stirring, under nitrogen, for three hours, cooled and methanol (4 ml) in tetrahydrofuran (10 ml) added carefully. The mixture was heated under reflux for one hour, cooled, hydrogen chloride gas passed and the mixture heated under reflux for one hour. After cooling and evaporation to dryness, the residue was dissolved in dilute hydrochloric acid, washed with diethyl ether, the aqueous phase made alkaline by addition of dilute aqueous sodium hydroxide and extracted with dichloromethane. The dichloromethane extracts were washed with brine, dried over anhydrous magnesium sulphate, filtered and the filtrate evaporated to dryness. The residual oil was purified by chromatography on silica gel using 2–3% methanol in dichloromethane as eluant. Conversion to its hydrochloride salt by addition of ethereal hydrogen chloride and recrystallisation from acetone-diethyl ether gave the title compound, m.p. 200–2° C., as a white solid.

$^1$H NMR (d$_6$-DMSO), ppm 1.25–1.35(6H,d), 2.9–3.15(2H,m), 3.25–3.55(3H,m), 3.9–4.2(2H,m), 4.45–4.55(1H,d), 6.15–6.30 (2H,s,exchanges with D$_2$O), 6.75–6.85(1H,d), 7.3–7.4(1H,dd), 7.45(1H,s), 10.65–11.00(1H, exchanges with D$_2$O).

EXAMPLE 7

2-[2,5-Difluorophenyl]-4-[1,1-dimethylethyl]morpholine hydrochloride

The title compound, m.p. 246–7° C. (methanol-ethyl acetate), was prepared from 2-[2,5-difluorophenyl]-4-[1,1-dimethylethyl]-5-oxomorpholine and borane-methyl sulphide by an analogous procedure to that described in Example 1.

$^1$H NMR (d$_6$-DMSO), ppm 1.4(9H,s), 3.0–3.25(2H,m), 3.35–3.6(2H,m), 4.1–4.4(2H,m), 5.5(1H,d), 7.2–7.55(3H,m), 11.75–12.0(1H,broad; disappears with D$_2$O).

EXAMPLE 8

4-[1,1-Dimethylethyl]-2-phenoxymethylmorpholine hydrochloride

The title compound, m.p. 134° C. (ethyl acetate), was prepared from 4-[1,1-dimethylethyl]-5-oxo-2phenoxymethylmorpholine and borane-methyl sulphide by an analogous procedure to that described in Example 1.

$^1$H NMR (d$_6$-DMSO), ppm 1.4(9H,s), 2.8-3.2(2H,m), 3.3-3.7(2H), 4.0-4.25(4H,m), 4.4(1H,m), 6.9-7.1(3H,m) 7.25-7.4(2H,m), 11.5(1H, exchanges with D$_2$O).

EXAMPLE 9

4-[2-Hydroxyethyl]-2-phenylmorpholine hydrochloride

A mixture of α-[[di-(2-hydroxyethyl)amino]methyl]-benzenemethanol (40g) and 48% aqueous hydrobromic acid (120ml) was heated under reflux for 2 hours, cooled, evaporated in vacuo and water added to the residue.

The pH was adjusted to 12 by addition of 10% aqueous sodium hydroxide and the mixture extracted with diethyl ether. The combined ether extracts were dried over anhydrous magnesium sulphate, filtered and evaporated to dryness. After purification by chromatography on silica gel using dichloromethane/methanol/0.88 ammonia (91:8:1) as eluant, the title compound was obtained by treatment with ethereal hydrogen chloride, m.p. 114-5° C., (methanol (trace)-ethyl acetate).

$^1$H NMR (d$_6$-DMSO+D$_2$O), ppm 2.93-4.3(10 H,m), 4.9-5.1(1H,dd), 7.3-7.6(5H,m).

EXAMPLE X5

4-[1,1-Dimethylethyl]-5-oxo-2-phenylmorpholine

The title compound, was prepared from α-[[[1,1-dimethylethyl]amino]methyl]benzenemethanol by an analogous procedure to that described in Examples X3 and X4. The product was purified by chromatography on silica using 0->8% methanol in dichloromethane as eluant.

$^1$H NMR (CDCl$_3$), ppm 1.5(9H,s), 3.3-3.7(2H,m), 4.3(2H,s), 4.7(1H,dd), 7.3-7.5(5H,m).

EXAMPLE X6

2-[3-Chlorophenyl]-4-[1-methylethyl -5-oxomorpholine

The title compound was prepared from 3-chloro-α-[[[1-methylethyl]amino]methyl]benzenemethanol by an analogous procedure to that described in Examples X3 and X4. The product was purified by chromatography on silica using 0->4% methanol in dichloromethane as eluant.

$^1$H NMR (d$_6$-DMSO), ppm 1.05-1.25(6H,dd), 3.05-3.75(2H,m), 4.25(2H,s), 4.55-4.95(2H,m), 7.35-7.7(4H,m).

EXAMPLE X7

2-(4-Amino-3,5-dichlorophenyl]-4-[1,1-dimethylethyl]-5-oxomorpholine

The title compound was prepared from 4-amino-3,5-dichloro-α-[[[1,1-dimethylethyl]amino]methyl 1]benzenemethanol hydrochloride by an analogous procedure to that described in Examples X3 and X4. The product was purified by chromatography on silica using 0->4% methanol in dichloromethane as eluant.

$^1$H NMR (d$_6$-DMSO), ppm 1.45(9H,s) 3.1-3.65(2H,m), 4.1(2H,s), 4.6(1H,dd), 5.5(2H, broad s, disappears with D$_2$O), 7.35(2H,s).

EXAMPLE X8

4-[1,1-Dimethylethyl]-5-oxo-2-[3-trifluoromethylphenyl] morpholine.

The title compound, m.p. 81-3° C., was prepared from 3-trifluoromethyl-α-[[[1,1-dimethylethyl]amino]methyl]b enzenemethanol hydrochloride by an analogous procedure to that described in Examples X3 and X4.

$^1$H NMR (d$_6$-DMSO), ppm 1.4(9H,s), 3.25-3.8(2H,m) 4.2(2H,s), 4.9(1H,dd), 7.6-7.95(4H,m).

EXAMPLE X9

2-[4-Amino-3-cyanophenyl]-4-[1-methylethyl]-5-oxomorpholine

The title compound was prepared from 4-amino-3-cyano-α-[[[1-methylethyl]amino]methyl]benzenemethanol by an analogous procedure to that described in Examples X3 and X4. The product was purified by chromatography on silica using 0->6% methanol in dichloromethane as eluant.

$^1$H NMR (d$_6$-DMSO), ppm 1.1-1.3(6H,d), 3.1-3.5(2H,m), 4.3(2H,s), 4.55-4.9(2H,m), 6.2(2H,s, exchanges with D$_2$O), 6.8-7.0(1H,d), 7.4-7.6(2H,m).

EXAMPLE X10

2-[2,5-Difluorophenyl]-4-[1,1-dimethylethyl]-5-oxomorpholine

The title compound was prepared from 2,5-difluoro-α-[[[1,1-dimethylethyl]amino]methyl]-benzenemethanol by an analogous procedure to that described in Examples X3 and X4.

$^1$H NMR (d$_6$-CDCl$_3$), ppm 1.4(9H,s), 3.1-3.7(2H,m), 4.3(2H,d), 4.9(1H,dd), 6.9-7.4(3H,m).

EXAMPLE 10

2-[2-Benzofuranyl]-4-(1,1-dimethylethyl]morpholine hydrochloride

2-[2-Benzofuranyl]-4-[1,1-dimethylethyl]-5-oxo-morpholine (2.25g) in dry diethyl ether (50ml) was added dropwise, with stirring, to a suspension of lithium aluminium hydride (0.344g) in dry diethyl ether (50ml). The mixture was stirred, under reflux, for 2.5 hours, cooled and water (0.35ml), 15% aqueous sodium hydroxide (0.35ml) and water (0.2ml) added carefully. After filtering, drying over anhydrous magnesium sulphate, refiltering and evaporation of the filtrate to dryness, the residual oil was converted to its hydrochloride salt by addition of ethereal hydrogen chloride. Recrystallisation from methanol-ethyl acetate gave the title compound, m.p. 214-6° C., as a white solid.

¹H NMR (d₆-DMSO), ppm 1.3–1.55(9H,s), 3.1–3.8(4H,m), 4.05–4.5(2H,m), 5.4–5.5(1H,d), 7.15(1H,s), 7.25–7.4(2H,m), 7.55–7.75(2H,m), 11.9(1H,broad; exchanges with D₂O).

EXAMPLE 11

4-[1-Methyl-2-phenylethyl]-2-phenylmorpholine hydrochloride

4-[1-Methyl-2-phenylethyl]-2-phenylmorpholine hydrochloride, m.p. 193–4° C. (methanol-ethyl acetate), was prepared, as a 45:55 mixture of diastereoisomers, from 4-[1-methyl-2-phenylethyl]-5-oxo-2-phenylmorpholine and borane-methyl sulphide by an analogous procedure to that described in Example 1.

¹H NMR (d₆-DMSO), ppm 1.2(3H,d), 2.5–3.8(7H,complex), 4.1–4.4(2H,m), 5.15(1H,broad d), 7.15–7.6(10H,m), 12.1(1H,broad, exchanges with D₂O).

EXAMPLE 12

2-[3-ChloroDhenVl]-4-[1,1-dimethyl-2-phenylethyl]-morpholine hydrochloride

The title compound, m.p. 235° C. (methanol-ethyl acetate), was prepared from 2-[3-chlorophenyl]-4-[1,1-dimethyl-2-phenylethyl]-5-oxomorpholine and lithium aluminium hydride by an analogous procedure to that described in Example 10.

¹H NMR (d₆-DMSO), ppm 1.30(6H,s), 3.05–3.8(6H,s on m), 4.15–4.5(2H,m), 5.25(1H,d), 7.2–7.65(9H,m), 11.8(1H,broad s, exchanges with D₂O).

EXAMPLE X11

2-[2-Benzofuranyl]-4-[1,1-dimethylethyl]-5-oxomorpholine

The title compound was prepared from α-[[[1,1-dimethylethyl]amino]methyl]benzofuran-2-methanol by an analogous procedure to that described in Examples X3 and X4. The product was purified by column chromatography on silica using 2% methanol in dichloromethane as eluant.

¹H NMR (CDCl₃), ppm 1.55(9H,s), 3.7(2H,m), 4.3(2H,s), 4.9(1H,t), 6.75(1H,s), 7.2–7.65(4H,m).

EXAMPLE X12

4-[1-Methyl-2-phenylethyl]-5-oxo-2-phenylmorpholine

The title compound was prepared from α-[[[1-methyl-2-phenylethyl]amino]ethyl]benzenemethanol by an analogous procedure to that described in Examples X3 and X4. The product, an oil, was purified by chromatography on silica using 0–>10% methanol in dichloromethane as eluant.

¹H NMR (d₆-DMSO), ppm 1.0–1.25(3H,complex), 2.65–3.6(4H,m), 4.15(2H,s), 4.5–4.9(2H,m), 7.05–7.55(10H,m).

EXAMPLE X13

2-[3-Chlorophenyl]-4-[1,1-dimethyl-2-phenylethyl]-5-oxo morpholine

The title compound was prepared, as an oil, from 3-chloro-α-[[[1,1-dimethyl-2-phenylethyl]amino]methyl]benzenemethanol by an analogous procedure to that described in Examples X3 and X4. The crude product was purified by chromatography on silica using 3% methanol in dichloromethane as eluant.

¹H NMR (CDCl₃), ppm 1.35(3H,s), 1.60(3H,s), 2.5–3.0(3H,m), 3.35–3.5(1H,d), 4.0–4.5(3H,m), 6.8–7.5(9H,m).

BIOLOGICAL EXAMPLES

Effects on Muscle Weights, Weight Gain and Feed Efficiency in Young Rats

Compounds were included in the diet of male Sprague-Dawley rats (initially about 50g body weight) for 6 days. There were nine rats in each treatment group housed in threes. Results are expressed relative to values for control groups of rats. The results for the compound of Example 1 are mean values from 12 experiments ±SD.

| Compound of Example No. | Level in Diet (ppm) | % Increase above Control Value | | | |
|---|---|---|---|---|---|
| | | Gastrocnemius + Plantaris Muscle Wt. | Soleus Muscle Weight | Weight Gain | Feed Efficiency |
| 1 | 5 | 25 ± 3 | 22 ± 5 | 17 ± 5 | 12 ± 7 |
| | 1 | 25*** | 26*** | 18** | 16** |
| 2 | 5 | 21*** | 24*** | 22*** | 23* |
| 3 | 5 | 25*** | 25** | 17** | 16** |
| | 1 | 30*** | 28*** | 9 | 12* |
| 4 | 5 | 23*** | 14** | 8 | 6 |
| | 1 | 5 | 11 | 12* | 8 |
| 5 | 50 | 11* | 5 | 13* | 2 |
| 6 | 5 | 24*** | 24*** | 15*** | 19** |
| | 1 | 18*** | 17* | 16** | 13 |
| 7 | 5 | 19*** | 7 | 17*** | 24*** |
| 8 | 5 | 9* | 1 | 5 | 4 |
| 9 | 5 | 16* | 29*** | 13* | 12* |

Significance of difference from control value (i.e. from 0):
*p < 0.05;
**p < 0.01;
***p < 0.001

Effects on body lipid content of rats

The compound of Example No. 1 was included in the diet of male Sprague-Dawley rats (initially about 50g body weight) for 6 days. There were nine rats in each treatment group housed in threes. The carcasses were dried and lipid was extracted into a chloroform/methanol mixture (2:1) for gravimetric estimation. Results are expressed relative to values for control groups of rats.

| Expt. No. | Level in diet (ppm) | % Reduction in body lipid content |
|---|---|---|
| 1 | 1 | 12* |
| 1 | 5 | 13* |
| 2 | 1 | 17* |
| 2 | 5 | 10* |

*Significant reduction in body fat relative to controls, P < 0.05.

We claim:

1. A compound of formula (IA), or a veterinarily or pharmaceutically acceptable acid addition salt thereof:

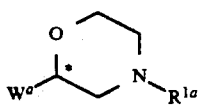
(IA)

wherein $R^{1a}$ is secondary or tertiary $C_{3-6}$ alkyl, and $W^a$ is phenyl, except when $R^{1a}$ is $C(CH_3)_3$ or $CH(CH_3)_2$, or phenyl substituted with at lest one of halogen, hydroxy, amino, cyano and trifluoromethyl but excluding compounds wherein $W^a$ is phenyl substituted with amino and at least one other subsituent selected from halogen, hydroxy, amino, cyano and trifluoromethyl.

2. A compound selected from the group consisting of 2-[3-chlorophenyl]-4-[1,1-dimethylethyl]morpholine, [4-[1,1-dimethylethyl]-2-[3-trifluoromethylphenyl]morpholine, 2-[2,5-difluorophenyl]-4-[1,1-dimethylethyl]-morpholine, 4-[1,1-dimethylethyl[-2-phenoxymethyl-morpholine, 2-[2-[benzofuranyl]-4-[1,1-dimethylethyl]-morpholine, and 2-[3-chlorophenyl]-4-[1,1-dimethyl-2-phenylethyl]morpholine, or a veterinarily or pharmaceutically acceptable acid addition salt thereof.

3. A pharmaceutical composition, comprising an effective non-toxic amount of a compound according to claim 1, and a pharmaceutically acceptable carrier therefor.

4. A method for increasing the weight gain and/or improving feed utilization efficiency and/or increasing the lean body mass and/or decreasing birth mortality rate and increasing post-natal survival rate of livestock, which method comprises the administration to livestock of an effective non-toxic amount of a compound of formula (IA), or a veterinarily or pharmaceutically acceptable acid addition salt thereof:

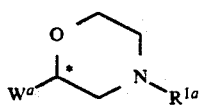
(IA)

wherein $R^{1a}$ is secondary or tertiary $C_{1-3}$ alkyl, and $W^a$ is phenyl optionally substituted by halogen, hydroxy, amino, cyano and trifluromethyl, with the proviso that (a) when $R^{1a}$ is $C(CH_3)_3$ then $W^a$ is phenyl having one of the substituents selected from amino or cyano.

5. A pharmaceutical composition, comprising an effective non-toxic amount of a compound selected from the group consisting of 2-[3-chlorophenyl]-4-[1,1-dimethylethyl] morpholine, 2-[4-amino-3,5-dichlorophenyl[-4-[1,1-dimethylethyl]morpholine, [4-[1,1-dimethylethyl]-2-[3-trifluoromethylphenyl]morpholine, 2-[4-amino-3-cyanophenyl[-4-[1-methylethyl]morpholine, 2-[2,5-difluorophenyl]-4-[1,1-dimethylethyl]morpholine, 4-[1,1-dimethylethyl]-2-phenoxymethylmorpholine, 2-[2-benzofuranyl[-4-[1,1-dimethylethyl]morpholine, and 2-[3-chlorophenyl]-4-[1,1-dimethyl-2-phenylethyl]morpholine, or a veterinarily or pharmaceutically acceptable acid addition salt thereof and a pharmaceutically acceptable carrier therefor.

6. A compound of formula (VA):

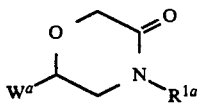
(VA)

wherein $R^{1a}$ is secondary or tertiary $C_{3-6}$ alkyl, and $W^a$ is phenyl optionally substituted by halogen, hydroxy, amino, cyano and trifluoromethyl with the proviso that (a) when $R^{1a}$ is $C(CH_3)_3$ then $W^a$ is substituted phenyl with one of the substituents being selected from halogen, hydroxy, amino, cyano and trifluoromethyl, and (b) when $R^{1a}$ is $CH(CH_3)_2$ then $W^a$ is substituted phenyl having at least one of the substituents selected from amino and cyano.

7. A method for increasing the weight gain and/or improving feed utilization efficiency and/or increasing the lean body mass and/or decreasing birth mortality rate and increasing post-natal survival rate of livestock, which method comprises the administration to livestock of an effective, non-toxic amount of a compound of formula (I), or a veterinarily acceptable acid addition salt thereof;

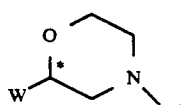
(I)

wherein $R^1$ is phenyl, $(C_{1-6})$ alkyl, $(C_{1-6})$ alkyl or hydroxy substituted $C_{1-6}$ alkyl and W is phenyl, optionally substituted by halogen, hydroxy, amino, cyano and trifluoromethyl, phenoxymethyl optionally substituted on the phenyl group, or benzofuran-2-yl.

8. A method for the treatment of conditions associated with an increased protein breakdown in humans, the enhancement of muscle function or the treatment of obesity in a human or non-human mammal, which method comprises the administration thereto of an effective non-toxic amount of a compound of formula (I) as defined in claim 7, or a veterinarily or pharmaceutically acceptable acid addition salt thereof.

9. A veterinarily acceptable formulation, for increasing the weight gain and/or improving the feed utilisation efficiency and/or increasing the lead body mass and/or decreasing birth mortality rate and increasing post-natal survival rate of livestock, or for use in the enhancement of muscle function or the treatment of obesity in a non-human mammal, which formulation comprises a compound of formula (I) as defined in claim 7, or a veterinarily acceptable acid addition salt thereof, and a veterinarily acceptable carrier thereof.

10. A formulation according to claim 9, comprising feedstuff or drinking water for livestock.

11. A formulation according to claim 9 in the form of a parenteral implant or sustained release rumen device.

* * * * *

UNITED STATES PATENT AND TRADEMARK OFFICE
CERTIFICATE OF CORRECTION

PATENT NO. : 5,082,840
DATED : January 21, 1992
INVENTOR(S) : Jonathan R. Arch et al It is certified that error appears in the above-identified patent and that said Letters Patent is hereby corrected as shown below:

Column 15, line 50, claim 4, after "cyano" add --and trifluoromethyl, and (b) when $R^{1a}$ is $CH(CH_3)_2$ then $W^a$ is phenyl having one of the substituents selected from amino and cyano--.

Signed and Sealed this

Twentieth Day of April, 1993

*Attest:*

MICHAEL K. KIRK

*Attesting Officer*     *Acting Commissioner of Patents and Trademarks*